United States Patent [19]

Mayo

[11] 4,294,225
[45] Oct. 13, 1981

[54] DIVER HEATER SYSTEM

[75] Inventor: Kenneth E. Mayo, Nashua, N.H.

[73] Assignee: Energy Systems Corporation, Nashua, N.H.

[21] Appl. No.: 41,537

[22] Filed: May 22, 1979

[51] Int. Cl.$^3$ ............................................. A61F 7/06
[52] U.S. Cl. .................................... 126/204; 126/208
[58] Field of Search ........................ 126/204, 208, 210

[56] References Cited

U.S. PATENT DOCUMENTS

| 3,513,824 | 5/1970 | Fitzgerald | 126/204 |
| 3,572,314 | 3/1971 | Teague | 126/210 |
| 4,068,651 | 1/1978 | Rappaport | 126/208 |
| 4,167,932 | 9/1979 | Zebuhr | 128/208 |
| 4,195,619 | 4/1980 | Hollen | 126/204 |

Primary Examiner—James C. Yeung
Assistant Examiner—Robert J. Marett

[57] ABSTRACT

High-pressure air from the air supply is admitted into the heater system through a pressure regulator. Fuel, such as propane, enters the system from a fuel canister. The air and fuel of controlled volumes mix and flow together into a catalytic combustion chamber where combustion is initiated by a spark generator. The heat of combustion is caused to pass through the walls of the combustion chamber, then through thermoelectric modules, converting part of the heat to electricity. The remaining and larger part of the heat passes to a heat exchanger on the opposite side of the thermoelectric module. Circulating water passes through the heat-exchanging chamber, absorbs the heat produced by the combustion reaction and is further pumped to the diver's suit. The electricity generated by the thermoelectric modules is used to power an electric motor driving a circulating pump.

6 Claims, 3 Drawing Figures

DIVER HEATER SYSTEM

RELATED APPLICATION

The subject matter of the present invention relates to Ser. No. 821,508, filed Aug. 3, 1977, in the name of Zebuhr et al.

BACKGROUND OF THE INVENTION

The present invention relates to apparatus for providing a warm water circulatory system for use in conjunction with diving suits and in particular to a heating system for warming the body of a diver while underwater.

The discomfort of a scuba-diver in cold water is obvious, and prolonged submersion in low-temperature conditions becomes intolerable and dangerous to the divers. Even with moderate surface temperatures, the cold at lower depths represents a forbiddingly restrictive factor limiting the scope, effectiveness, and freedom of the diver's range and ability to do useful work.

In the aforementioned application of Zebuhr et al, a diver heater system has been disclosed having a catalytic combustion chamber in association with a fluid heat exchanger. High pressure air is employed to control a fuel pressure regulator and a pneumatic pump for supplying a mixture of air and fuel to the combustion chamber and for circulating water through the heat exchanger. While this heater is quite efficient, the use of the air pressure to provide a pneumatic pump results in certain operational limitations to the depth at which the heater can be used. Further, the circulation of water through the heater is not efficiently effected and does not provide efficient means for forming a closed fluid loop by which the heated water can easily return from the diver's suit to the heater.

These and other objects are fully realized in the present invention, as will become apparent from the ensuing sections of this specification.

SUMMARY OF THE INVENTION

The diver heater system herein described operates by heating a circulating fluid such as water and delivering the warmed water to the diver's suit via a closed loop tubulated undergarment worn under the diver's insulating diving suit. This is accomplished by utilizing some of the high-pressure air from the diver's self-contained underwater breathing apparatus (scuba) air tank or air from a separate tank to serve as a combustion medium for fuel from an accompanying fuel tank. The heat of combustion of the fuel is transferred to the pump-circulated water via a thermal path including thermoelectric modules which convert a small part of the heat to electricity to operate an electrically driven water-circulating pump.

High-pressure air from the scuba air tank's first stage regulator is carried by a pressure hose into the diver heater system's air regulator. A fuel intake regulator introduces suitably proportioned amounts of fuel (e.g. propane.) Both air and fuel pass through volume adjusting orifices into a common duct in which they mix and flow together into a catalytic combustion chamber, where ignition is initiated by a spark generator and combustion occurs. At the same time, the water in the system is circulated by the electric motor driven circulating pump through a heat exchange chamber surrounding the catalytic combustion chamber. Thermoelectric modules are interposed between the combustion chamber walls and said heat exchanger chamber walls such that one side of the thermoelectric modules is maintained hot, the other side cool, heat exchange is accomplished, and the warmed water is pumped further through a short umbilical line into the diver's suit. Electric power generated by the thermoelectric module is directed to an electric motor driven circulating pump which forces the water through the aforementioned fluid passages. Provision is made for exhausting the products of combustion from the combustion chamber to the ambient water.

Preferred embodiments of the diver heating system, including the best mode now contemplated of carrying out the concepts of this invention, will now be described in full, clear and concise detail with reference to the accompanying drawings.

DESCRIPTION OF THE INVENTION

Figure 1:
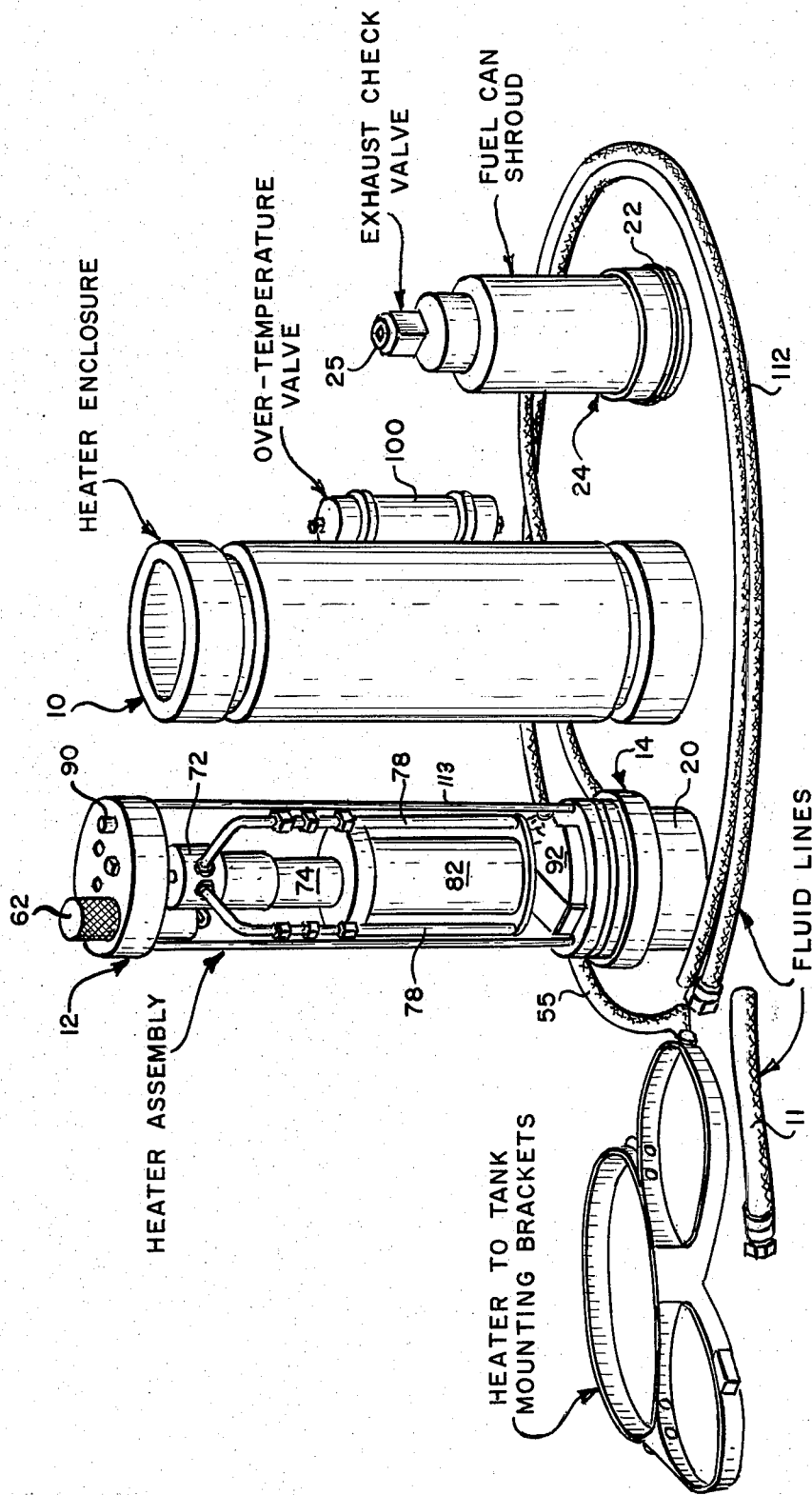
FIG. 1 is a perspective view of the diver heater assembly constructed in accordance with this invention, with its associated umbilical connection to the air supply and diver's suit.
Figure 2A:
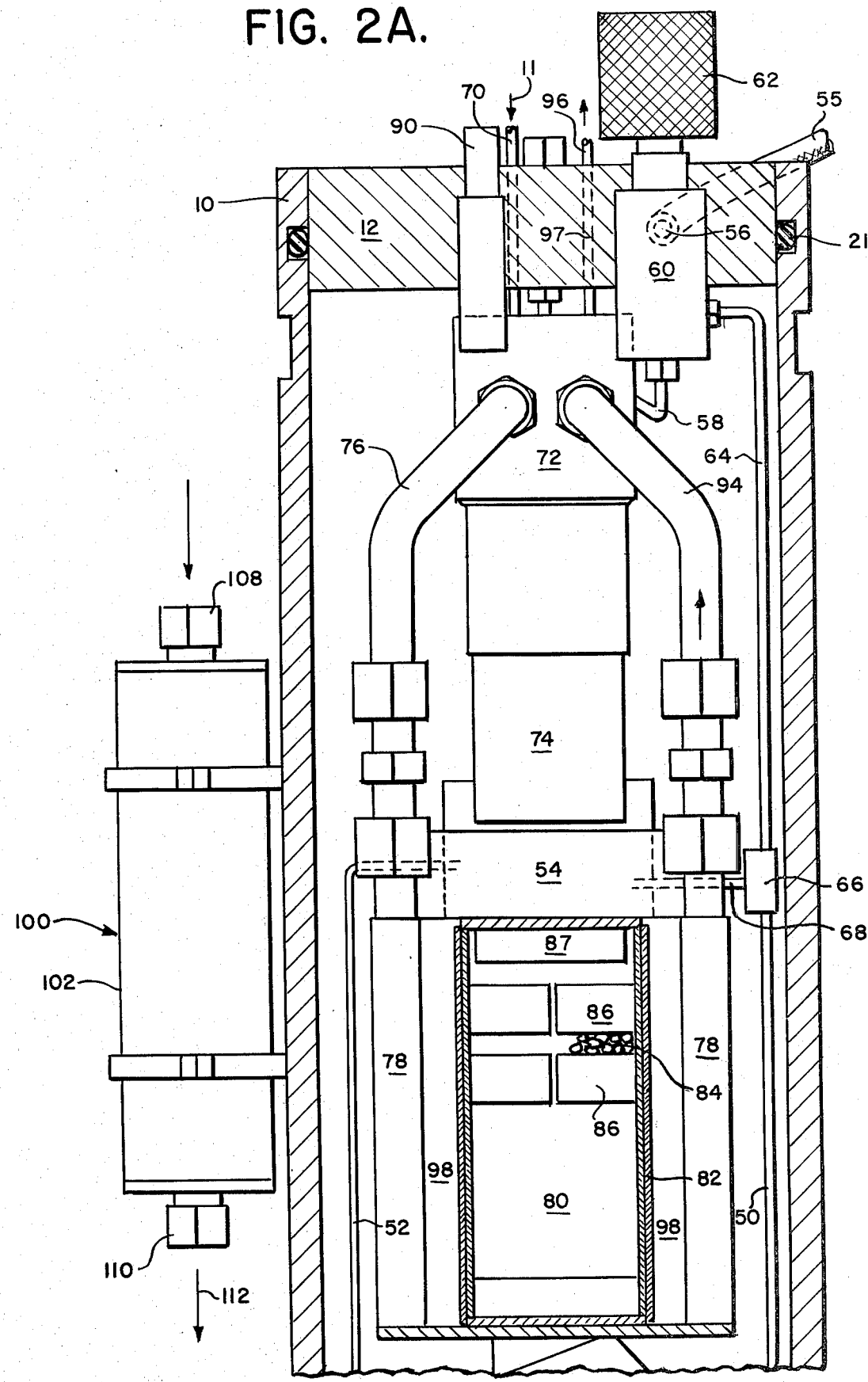
FIGS. 2A and 2B are combined forms and enlarged longitudinal cross-sectional view of the diver heater assembly of FIG. 1.
Figure 2B:
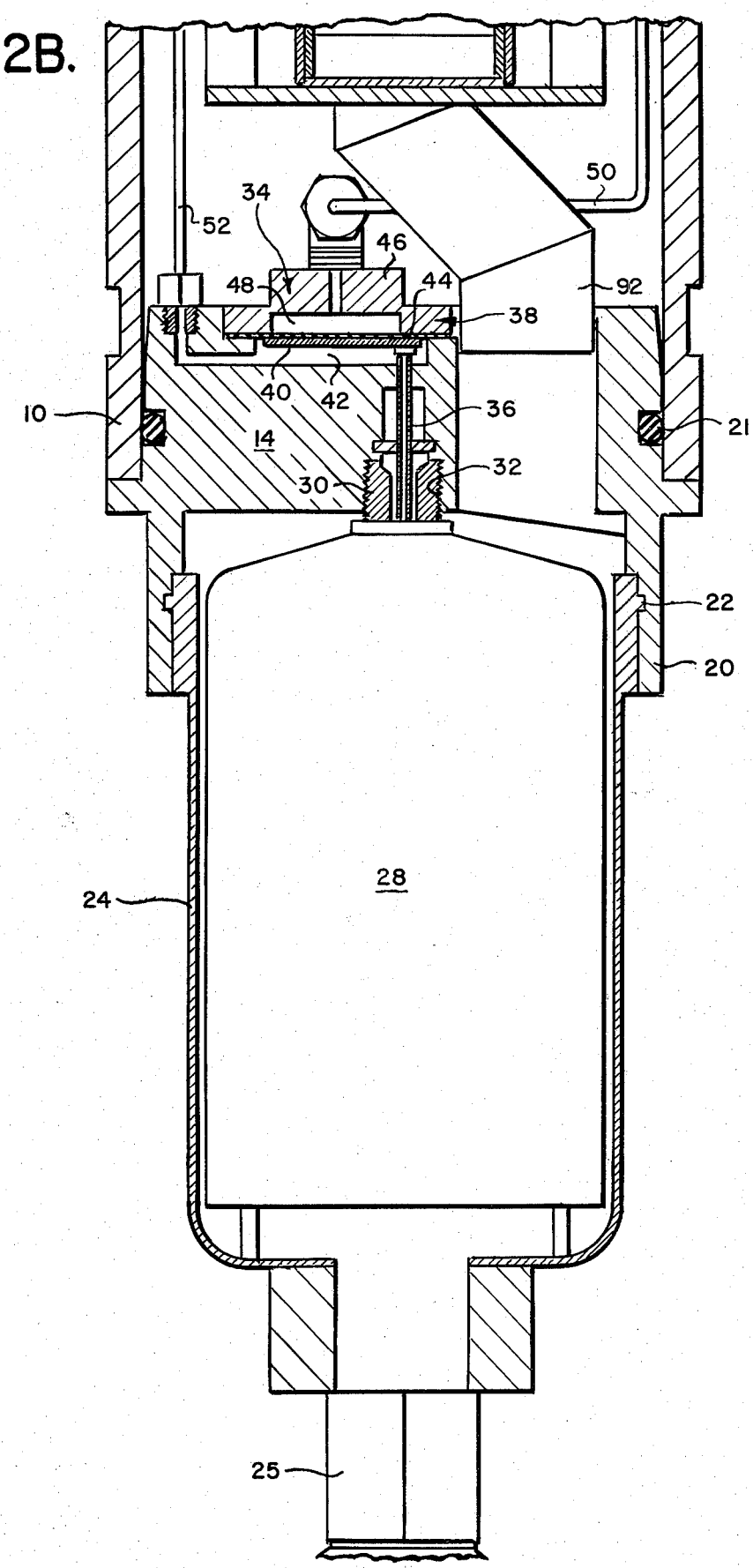

As seen in the drawings, the diver heater unit of the present invention is enclosed in a supporting cylindrical frame 10 enclosed at each end by end caps 12 and 14 sealed by O rings 21, respectively. The frame is provided with suitable straps and harness for attachment to the diver's body or to the normal scuba equipment worn by the diver. The lower end cap 14 is provided with a suitable flange allowing it to be seated at the end of the cylinder. Longitudinal tie rod members 113, connecting the end caps hold the upper end cap 12 properly in place, thus, forming a water tight enclosure within the cylindrical frame.

The lower end cap 14 is provided with an annular skirt 20 having a groove 22 on its inner surface, which is adapted to receive a shroud 24 provided with corresponding detents. The skirt is provided with axial slots permitting entry of the detents which can then be rotated into a fixed position within the groove 22 in a manner of a bayonet fixture. Alternatively the skirt and the shroud can be provided with mating screw means. Suitable seal means may also be provided between the skirt and the shroud.

The shroud 24 is adapted to receive a propane fuel canister 28 which is screwed at its neck 30 into a receiving bore 32 formed within the lower end cap 14. The shroud 24 is somewhat larger in diameter than the canister 28 leaving room about the canister for circulation of exhaust gases produced during operation of the diver unit. The outer end of the shroud is enclosed by a bottom wall in which is located an adjustable check valve 25 permitting the exhaust of gas. The check valve, for example, may be a spring loaded ball valve permitting the exiting of exhaust gas, but not entry of water.

A fuel inlet valve generally depicted by the numeral 34 comprises a movable hollow, needle-like stem 36 having one end inserted within the fuel canister 28 and the other end feeding to a fuel supply regulator generally depicted by the numeral 38, having a floating plate 40 against which the needle abuts. The floating plate 40 is located in a cavity 42 formed in the end cap. Mounted above the floating plate is a diaphragm 44 secured about its edges between an annular shoulder formed in the end cap and a removable cover member 46 which is shaped to provide a second cavity 48 above the diaphragm to which air under pressure is fed from a conduit 50.

The fuel regulator is similar to that disclosed in the aforementioned application of Zebuhr et al and functions so that when air enters the chamber 48, it exerts a pressure against the diaphragm 44 which acts against the moveable plate 40 which in turn depresses the fuel valve stem 36 allowing fuel to emerge from the fuel tank into the cavity 42 until the diaphragm is restored and the valve stem is released. The fuel in the cavity is then passed via a conduit 52 into a manifold orifice block 54.

Air is introduced from a high pressure source such that air supply of the scuba gear normally worn by the diver via an umbilical hose 55 connected to an inlet 56 located in the upper end cap 12 of the housing. The inlet 56 communicates via a conduit 58 to an adjustable air regulator 60, controlled by a knob 62. The air from the regulator is passed via a conduit 64 to a coupling 66 where it is separated into two streams passing through conduit 50 into the fuel regulator and a conduit 68 into the fuel-air mixing block 54.

Ambient or recirculated water, as the case may be, enters through an inlet 70 in the upper end cap 12, where it passes into a circulating pump 72 operated by an electric motor 74. The water is pumped under pressure from the pump through piping 76 into heat exchanges 78 surrounding a combustion chamber 80 located below the mixing block 54. The heating chamber is composed of a housing 82 in which is located catalytic material 84 in pelletized form such as platinized pellets or alumina pellets coated with black platinum catalyst. The pellets 84 are separated by a plurality of fins 86 arranged in a manner to permit uniform circulation of the fuel-air mixture and to aid heat transfer from the catalyst bed to the outer walls of the combustion chamber 82. The fuel and air is fed in a desired ratio through the orifice block 54 and mixed within a mixing block 87 and fed directly into the combustion chamber via one or more orifices. An ignition system comprising a piezoelectric spark generator unit 90 is mounted in the upper cap 12 with electrodes passing into the combustion chamber, so that after the mixed air and gas is introduced into the combustion chamber, a suitable ignition is provided. The combusted gaseous or waste product of combustion exits from the lower end of the heating chamber via a duct 92 through the lower end cap 14 into the shroud 24. The heat of combustion is thrust outward through the wall 82 of the combustion chamber into contact with the heat exchanger 78. Thus the heated water is returned to the pump via return pipe 94 whence it is forced by the pump through an outlet 96 also located within the upper end cylinder.

Interposed between the combustion chamber 8 and the annular heat exchanger 78 are a plurality of thermo-electric units 98 capable of converting heat directly into electrical energy. The thermo-electrical units are preferably formed of bismuth tellerite available through the TELEDYNE CORPORATION. They are connected in series to the pump motor thereby supplying to the motor the necessary power to operate the water pump.

The heated water passes from the outlet 96 through a small bore 97 to an over-temperature valve 100, which is mounted on the exterior of the housing. The over-temperature valve is preferably of the type disclosed in the application of John E. Six, entitled "Over-Temperature Valve", filed on even date herewith. The heated water enters the cylinder through an inlet 108, and exits through the outlet 110, into suitable umbilical piping 112 connected to the diver's uniform. When the heated water passing through the valve exceeds a predetermined temperature level, it is automatically cooled to a proper temperature. Reference to the Six Application is made for the details of the over-temperature valve and the same is incorporated herein as if more fully set forth. The piping 112 to the diver's uniform preferably includes a return pipe 11 connected to the water inlet 70 in the upper cap 12 of the housing, so that the heated water effluent from the diver's uniform can be recirculated.

The provision of the over-temperature gauge and valve permits the use of the present diver heater system in an entirely closed water recirculating system. That is the heated water may pass directly into the body suit of the diver and once used therein be recirculated back into the diver heater unit. Thus, completely cold ambient temperature of the water is not introduced into the heat exchanger and the combustion cycle is more efficiently operated with consequent reduction in the use of fuel. The over-temperature sensor and valve controls the temperature of the circulating water and permits the introduction of ambient water once this water reaches an under-excess temperature. Such excess temperature can occur by evaporation or boiling off of the heated water or through a malfunction of some kind.

A further advantage of the present invention lies in the use of the thermo-electric units 98. These units are capable of producing an amount of electricity sufficient to power the motor of the pump, eliminates the need for umbilical connection and/or the use of the previous hydraulic pumping systems. The electric power thus produced has often been greater than that required for pumping and thus is also capable of providing other functions such as powering a flashing xenon lamp to help divers locate one another of for powering various electronic circuits such as communication devices.

A still further advantage of the present invention lies in mounting the fuel canister in an enclosing shroud through which the exhaust gases pass from the combustion chamber. The exhaust gases heat the fuel within the canister and maintain the fuel at proper pressure levels even at great depths in the ocean, thus permitting the diver to go to greater depths in the ocean not hitherto possible and providing a unit not limited to use of propane as a fuel, nor limited to air as an oxidizer.

A still further advantage of the present invention lies in the fact that the entire unit except for the overtemperature control is located within a small cylindrical cylinder capable of being carried on the back of the diver without any difficulty and without any interference with the normal air supply or the diver's freedom of movement. The temperature gauge itself is a rather small unit and likewise does not interfere with the diver.

A still further advantage lies in the fact that the present unit may be used primarily in a closed system circulating ambient water although it may be used as well in an ambient water inlet system. A suitable inlet valve can be used to feed ambient water as the heatable media.

The diver heater system herein described may be used to deliver heated water to the diver in any one of the following three ways:

1. Closed Loop: A completely closed system is used, wherein the heated water is delivered to and passes through a tubulated garment worn by the diver inside a dry diving suit, then is recirculated through the heater system.

2. Semi-Closed Loop: The bulk of the water delivered to the diver's wet suit is recirculated through an umbilical line back to the heater system. Water lost in the process is replaced by ambient cold water through the overtemperature valve.

3. Open Loop: Water is drawn from the ambient, heated, delivered into the diver's wet suit. After being distributed over the diver's body through a perforated tube within the wet suit and circulated by the diver's swimming motions, the water is returned to the ambient.

The diver's heating system described herein provides for a range of heat output rates to accommodate diving heating conditions at varying depths and varying water temperatures. In order to prevent possible diver injury from missetting of heating rate, the temperature controlled valve is provided in the heated water line leaving the heat exchangers. This valve will automatically open and vent a portion of heated water, replacing that amount with ambient water if the water leaving the heat exchanger should exceed a preset maximum temperature.

The following performance characteristics and dimensions offer a general idea of the capacity, effectiveness and compactness of the diver's heating system: Using approximately 20 SCFH of air or helium-oxygen mixture from a scuba air tank at 125–145 psig and a six-ounce canister of propane fuel, the system provides 1500 BTU per hour (435 thermal watts) in the form of heated water, with a fuel consumption rate of about 1.6 ounces of propane per hour. Thus, 3¾ hours of heating are available per fuel canister. At a water flow rate in the range of 0.3 gallons per minute through the system and at a depth of 30 feet, a water temperature increase of at least 10 degrees Fahrenheit is achieved.

The entire diver heater unit, including the fuel canister is about 4½ inches in diameter, about 18 inches long, and weighs in the range of 14½ pounds. The unit, therefore, represents a relatively insignificant increase in the encumbrance of a scuba diver's equipment. It has a net negative buoyancy of 4½ pounds.

Various modifications, embodiments, and changes have been suggested in the foregoing disclosure. It will be clear that other modifications and changes may also be made. It is intended, therefore, that the present disclosure be taken as illustrative only and not limiting in the scope of the invention.

What is claimed is:

1. A heater for warming the body of a diver while under water comprising a housing, having a fluid inlet, a combustion chamber, means for supplying air and means for supplying fuel to said chamber of combustion therein, and means for exhausting the products of combustion, a fluid heat exchanger arranged in association with said combustion chamber, a pump for circulating fluid through said heat exchanger to be heated, electric motor means for operating said pump, and thermoelectric means mounted in association with said combustion chamber for converting a portion of said heat to electrical energy and means for passing said electrical energy to said motor to operate said pump, said pump having means for passing the heated fluid to the diver said means for supplying said fuel comprises a fuel storage canister removably securable to said housing in combination with the exhaust means from said combustion chamber to cause said fuel storage canister to be heated by said exhaust.

2. The heater according to claim 1 including means for adjustably regulating the flow of exhaust.

3. The heater according to claims 1, including a temperature controlled valve means for cooling heated water exiting from said heat exchanger means when said heated water is in excess of a predetermined temperature.

4. The heater according to claim 3, including a diver underwater suit having means for the passage of water therethrough in conduction proximity to said diver's skin, said suit having means for connection to said water conduit means.

5. The heater according to claim 1, including means for mixing said air and fuel for induction to said combustion chamber, air flow regulator means for adjusting the volume of said air before entering to said mixing means, and fuel flow regulating means for adjusting the volume of said fuel before entry of said fuel to said mixing means.

6. The heater according to claim 5, including combustion-catalytic material contained within said combustion chamber.

* * * * *